(12) United States Patent
Hanson et al.

(10) Patent No.: US 6,821,419 B2
(45) Date of Patent: Nov. 23, 2004

(54) DIFFUSION CELL WITH QUICK RELEASE CLAMP

(75) Inventors: Royal A. Hanson, Westlake Village, CA (US); Bruce E. Renslow, Castaic, CA (US); Steven W. Shaw, Thousand Oaks, CA (US); Jerome S. Elkins, Dallas, TX (US)

(73) Assignee: Hanson Research Corporation, Chatsworth, CA (US)

( * ) Notice: Subject to any disclaimer, the term of this patent is extended or adjusted under 35 U.S.C. 154(b) by 308 days.

(21) Appl. No.: 10/056,186

(22) Filed: Jan. 28, 2002

(65) Prior Publication Data

US 2003/0144626 A1 Jul. 31, 2003

(51) Int. Cl.[7] ............................................... B01D 65/08
(52) U.S. Cl. ....................................................... 210/297
(58) Field of Search .................................... 210/297, 319, 210/321.63, 321.84, 321.75; 73/38, 64.47

(56) References Cited

U.S. PATENT DOCUMENTS 5,198,109 A * 3/1993 Hanson et al. ......... 210/321.75
5,296,139 A * 3/1994 Hanson et al. .............. 210/297

* cited by examiner

*Primary Examiner*—Kevin T. Truong
(74) *Attorney, Agent, or Firm*—Jack C. Munro

(57) ABSTRACT

A diffusion cell to facilitate the automatic or manual removal of test aliquots of liquid from a receptor chamber of the diffusion cell so as to determine percantaneous absorption through a membrane of a substance from a donor chamber into a receptor chamber of the diffusion cell. There is utilized a capillary port through which the test aliquot is to be removed. A refilling tube connects also with the receptor chamber to add receptor liquid into the receptor chamber as the test aliquot is being removed. A quick release clamping apparatus secures the donor housing which contains the donor chamber tightly to the main housing of the diffusion cell.

13 Claims, 2 Drawing Sheets

DIFFUSION CELL WITH QUICK RELEASE CLAMP

BACKGROUND OF THE INVENTION

1. Field of the Invention

The field of this invention relates to testing equipment and more particularly to an apparatus which is usable to determine the transfer of a substance through a membrane into a liquid placed in contact with the opposite side of the membrane.

2. Description of the Related Art

There are three ways to apply a medicine to the body of any animal. The most common way probably is to take the medicine orally. The second most common way is direct injection by using a syringe. The third way, which is becoming more common, is by permutation of the drug through the skin.

It is well known to utilize a cream or ointment to be placed on one's skin for the treating of a disease of the skin. However, what is becoming more common is the use of a drug in the form of an ointment, cream or patch that is to be placed onto the skin for the purpose of the drug entering the human body for the treatment of a medical condition. Transdermal patches are being commonly used, at the present time, for the administration of nitroglycerine for heart patients as well as the applying of nicotine to individuals for the purpose of assisting individuals in stopping smoking.

The usage by human beings and other animals of any topically applied medication depends on the specific knowledge of the transfer kinetics of the active ingredients of the medication on its ability to penetrate through the skin and be absorbed by the animal's body. It is necessary to know exactly the amount of active ingredients that will penetrate the animal's skin within a given amount of time. This information is essential to determine the amount of the dosage of medicine to be applied to the skin patch or the amount of ointment or cream that is to be applied to the animal's skin.

In the past, it has been common to utilize a vertical diffusion cell which is commonly called a Franz cell, named by it's inventor. The Franz cell is in the form of a container with the upper half separated from the lower half by a porous membrane comprising a barrier. A donor material is placed against the membrane. A receptor fluid, such as a saline solution, is placed within a receptor chamber of the Franz cell container. At predetermined intervals, aliquots are withdrawn from the receptor fluid. Each aliquot is then tested to determine the amount of active medicine that has been absorbed by the receptor fluid.

Generally, the testing of the receptor fluid occurs over a period of hours or days with each sample aliquot withdrawn at certain time intervals apart. Typically, a typical testing apparatus will utilize a plurality of the Franz cells from which there will be automatically removed aliquots from each Franz cell with the aliquot then being tested to determine the quantity of medicine that has been absorbed by the receptor fluid. The reason that a plurality of Franz cells are used is to provide a plurality of readings for the particular donor substance so then an overall average can be arrived at and make a determination of the transfer characteristics of the active ingredients of the donor substance into the receptor fluid. The donor substance could comprise a solid, semi-solid, cream, gel or liquid. Typical donor substances are creams, topical ointments, lotions, or transdermal patches. The active ingredient in the donor substance could comprise a medicine such as an antibiotic or an ophthalmic preparation, cosmetic, pesticide, paint or any potentially toxic substance that would have a tendency to penetrate an animals skin. The receptor fluid normally comprises a saline solution, water or buffered solution. The aliquots, which are to be removed from the receptor fluid, are defined as an exact sub-volume of the overall volume of the receptor fluid.

Generally useful in the whole field of physical chemistry, Franz cells have become particularly useful in the health care field. Transfer kinetics of active substances through the animal skin are determined in order to determine the level of epidermal exposure to pesticides, chemicals, ointments, cosmetics, paints and other substances.

The membrane that is used in conjunction with the Franz cell could comprise cadaver skin or some form of a synthetic membrane that is specifically constructed to essentially duplicate human skin.

SUMMARY OF THE INVENTION

One of the objectives of the present invention is to construct a diffusion cell which provides for the withdrawal of aliquots in a manner that does not permit air to be added into the receptor chamber.

Another objective of the present invention is to construct a diffusion cell which provides for accurate replacement in volume of fresh receptor fluid equal to what was withdrawn in each aliquot.

Another objective of the present invention is to construct a diffusion cell which minimizes the volume of the aliquot that is contained within the sampling port thereby having minimal affect on the subsequent aliquot that is withdrawn.

Another objective of the present invention is to incorporate luer fittings in conjunction with the sampling port and refilling port for the receptor fluid which provides for easy connection and disconnection with a withdrawing conduit and a refilling conduit at the same time achieving a leakage free connection.

Another objective of the present invention is to utilize a quick disconnect clamping apparatus in conjunction with the diffusion cell to insure that the donor housing is tightly secured to the main housing of the diffusion cell.

The basic embodiment of diffusion cell of the present invention utilizes a main housing of a container which has a receptor chamber. The receptor chamber has an open top and a closed bottom. A receptor liquid is to be located within the receptor chamber in a sufficient quantity so as to connect with the open top. A receptor liquid refilling port connects with the receptor chamber with this refilling port being located directly adjacent the closed bottom. A sampling port connects with the receptor chamber intermediate the open top and the closed bottom but nearer the open top. A thin membrane is mounted on the main housing extending across the open top effectively closing such. A donor housing has a donor chamber which connects with the membrane. A media is to be supplied to the donor chamber and in contact with the membrane. A quick release clamping apparatus engages with the donor housing function to tightly press the donor housing onto the membrane and the main housing.

A further embodiment of the present invention comprises the main embodiment where the sampling port includes a capillary tube so as to minimize the volume of receptor fluid that is contained within the sampling port upon withdrawing of an aliquot.

A further embodiment of the present invention is where the main embodiment is modified by the donor housing comprising a disc with a center opening which forms the donor chamber. A cover plate is designed to be located over the disc with a cap to be mounted over the cover plate.

A further embodiment of the present invention is where the just previous embodiment is modified by the cap including a viewing port to facilitate visual observation of the receptor chamber in the area of the open top.

A further embodiment of the present invention is where the basic embodiment is modified by the sampling port and the refilling port both having mounted thereon LUER fittings.

A further embodiment of the present invention is where the clamping apparatus is utilized in conjunction with the diffusion cell comprises a pair of plates that define an internal cavity. The main housing is to be inserted within this cavity. One of the plates is mounted against the cap of the donor housing with the other of the plates being fixed to the main housing. A spring biasing arrangement connects between the plates of the clamp of the clamping apparatus therefore tending to maintain a tight connection by the clamping apparatus between the main housing and the donor housing.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE INVENTION

Figures 1, 2:
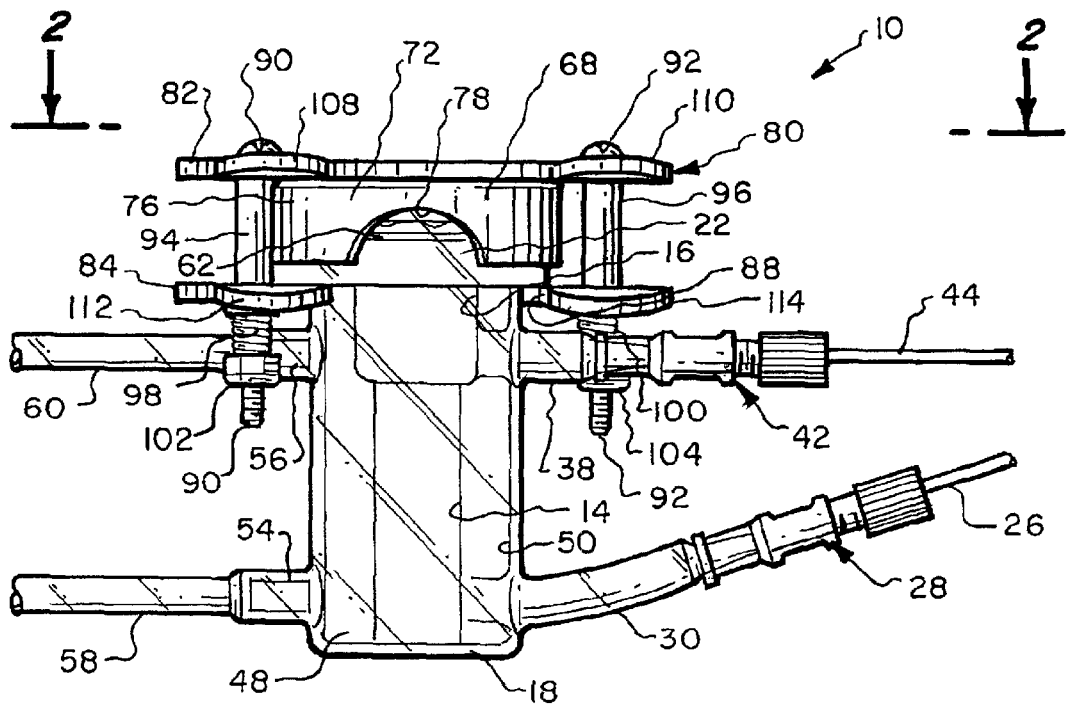
FIG. 1 is an exterior side view of the diffusion cell of the present invention.
FIG. 2 is a top plan view of the diffusion cell of the present invention taken along line 2—2 of FIG. 1.
Figure 3:
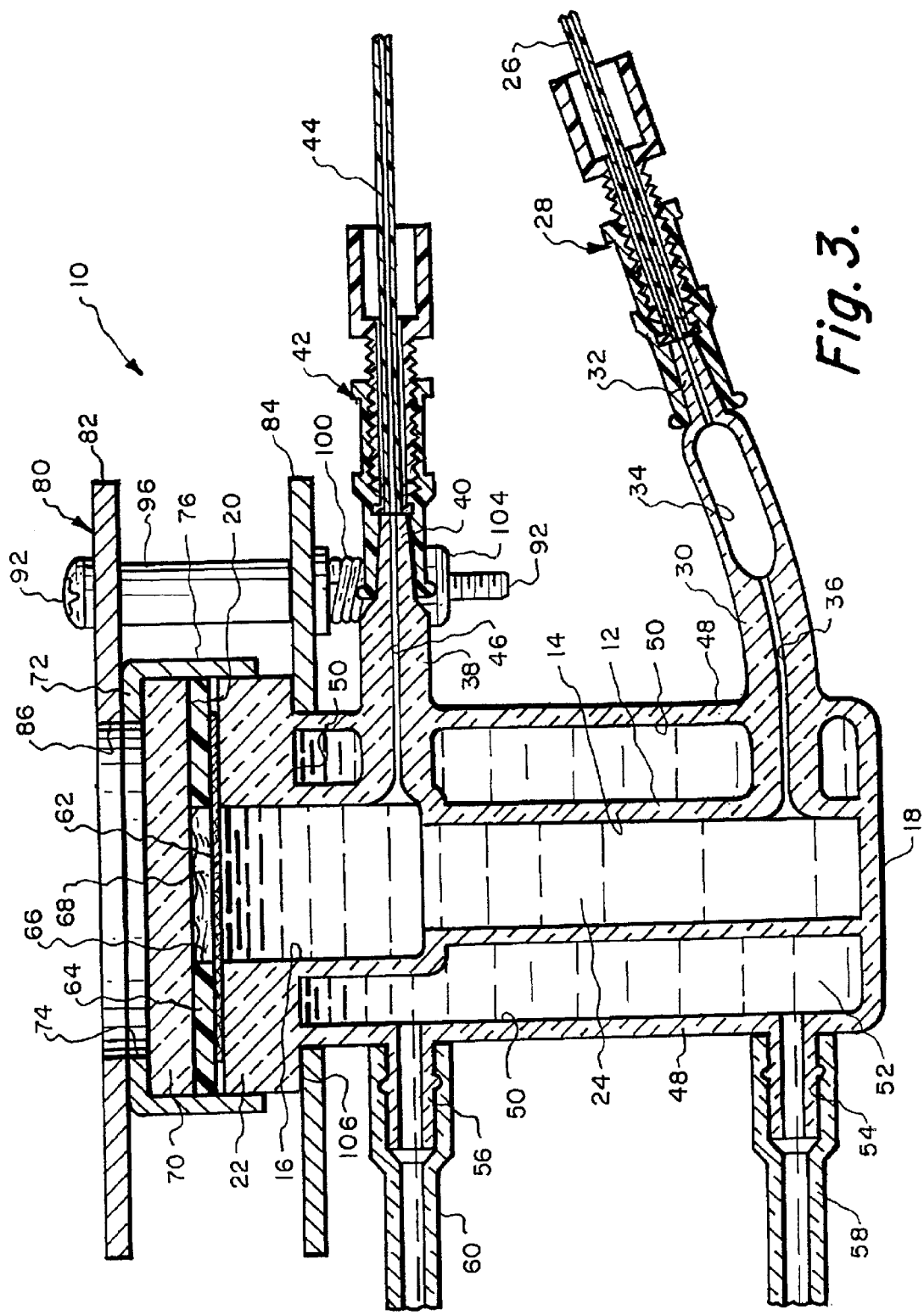
FIG. 3 is a longitudinal cross-sectional view through the diffusion cell of the present invention taken along line 3—3 of FIG. 2.

Referring particularly to the drawings, there is shown the diffusion cell 10 of this invention. The diffusion cell 10 includes a thin walled receptor container 12. The container 12 will normally be constructed of glass. Located internally of the receptor container 12 is a receptor fluid chamber 14. The upper portion 16 of the receptor fluid chamber 14 is expanded to be of a greater diameter than the lower portion of the chamber 14. The diffusion cell 10 has a closed bottom 18 and an open top which is located at flat surface 20 which is formed on annular flange 22. The receptor fluid chamber 14 is designed to be filled with receptor liquid 24. The receptor liquid 24 will normally comprise water, saline or some other type of liquid solution.

Liquid is to be supplied into the receptor fluid chamber 14 by means of a refilling conduit 26 which connects by a refilling connector 28 through a refilling tube 30. Refilling tube 30 has a LUER fitting 32. The LUER fitting 32 is capable of quickly being disconnected and connected to the refilling connector 28, and when it is connected to the refilling connector 28, there is established a secure leakage free connection. The LUER fitting 32 is basically tapered and has an exterior roughened surface which facilitates the forming of the leakage free connection. Formed within the refilling tube 30 is a storage chamber 34. From the storage chamber 34, liquid is to be supplied through capillary passage 36 to the receptor fluid chamber 14. The function of the storage chamber 34 is to provide an area for collection of any air bubble and to prevent that bubble from entering into the receptor fluid chamber 14.

It is to be noted that the refilling tube 30 connects to the receptor fluid container 14 directly adjacent the bottom 18. This means that new receptor fluid 24 is always being supplied into the receptor fluid chamber 14 as far away from the open top as possible. The reason for this is so that the new receptor fluid 24 that is being supplied will not immediately intermix with the aliquot or sample of fluid that is being extracted from the upper portion 16 by the sample tube 38. The sample tube 38 terminates in a LUER fitting 40 which connects with a sampling connector 42. Sampling connector 42 connects with the a sampling conduit 44. The sampling tube 38 has a capillary passage 46 through which the aliquot that is to be removed is to be conducted prior to entrance within the sampling conduit 44.

It is desirable that at the time each aliquot is removed that the liquid of the aliquot be representative of the precise percentage of the amount of active ingredient that is contained within the receptor liquid 24. Inherently, because there will always be some small amount of residual aliquot liquid contained within the capillary passage 46 and also contained within the sampling conduit 44, it is desirable to have the smallest amount of residual aliquot liquid contained within the passage 46 and the conduit 44. Residual aliquot liquid contained within the passage 46 and the conduit 44 is not representative of the receptor liquid. Therefore, because there is a minimal amount of residual aliquot liquid, only a small waste volume is required to purge the residual volume and the reading that is taken on the particular selected aliquots should give a true representation of the amount of active ingredients within that aliquot since the volume of the previously obtained aliquot that is being added to the new aliquot constitutes only a minor amount of the total volume of the aliquot since the volume of the capillary passage 46 constitutes only a minor amount of the total volume of the aliquot. It is to be understood that the capillary passage 46 will not be completely filled as most of the liquid that remains within the capillary passage 46 will be drained back into the receptor fluid chamber 14.

Surrounding the receptor container 12 is a jacket 48. The jacket 48 is also formed of glass and is to normally be constructed integral with the receptor container 12. Between the receptor container 12 and the jacket 48 is located a jacket chamber 50. Jacket chamber 50 is basically annular and totally surrounds the receptor container 12. It is desirable, and actually necessary, for the receptor liquid 24 to be maintained at a known temperature. A temperature maintaining liquid 52 is to be supplied within the jacket chamber 50 and is intended to circulate through the jacket chamber 50 from an inlet tube 54 to an outlet tube 56. An inlet conduit 58 is connected to the inlet tube 54, and an outlet conduit 60 is connected to the outlet tube 56. A flow of the liquid 52 is to constantly be supplied from the inlet conduit 58 to the jacket chamber 50. A similar quantity of the liquid 52 will also be discharged through the outlet conduit 60. It is to be understood that the inlet conduit 58 and outlet conduit 60 will be connected to a source of the liquid, which is not shown. Generally, at this source of liquid there will be located some type of a heater that will be designed to raise the temperature to a certain temperature to correspond to the temperature level of the particular animal for which the diffusion cell 10 is to be used. For example, in the case of a human, the temperature level of the liquid 52 should be thirty-two degrees centigrade. It can quickly be seen that the temperature of the liquid 52 will readily pass through the receptor container 12 with the result that the receptor liquid 24 will also be located at the same temperature as the liquid 52.

A membrane 62 is to be placed on the flat surface 20. The function of the membrane 62 is to essentially duplicate human skin or the skin of whatever animal the diffusion cell 10 is being used. The membrane 62 could comprise cadaver skin, a synthetic material that essentially duplicates human skin, some form of a plastic membrane and even possibly a tightly woven cloth material. On the membrane 62 is located a donor plate 64. The donor plate 64 is in the shape of a washer having a center opening 66. Typically, the donor plate 64 will be constructed of glass, plastic or other rigid material. With the donor plate 64 located against the membrane 62, the membrane 62 is clamped between the donor plate 64 and the flat surface 20 of the annular flange 22. Within the opening 66 is to be located a quantity of donor material 68. Typically, the donor material 68 will be in the form of an ointment or cream but could comprise a liquid and possibly even a solid material such as a gel. The donor material 68 will be in contact with the upper surface of the membrane 62. The lower surface of the membrane 62 will be in continuous contact with the receptor liquid 24. It can thus be seen that the active ingredients of the donor material 68 will penetrate the membrane 62 and become mixed within the receptor liquid 24 and extraction of aliquots over a period of time through the capillary passage 46. The amount of active ingredients within the donor material 68 within each aliquot is to be measured by an appropriate measuring apparatus, which is not shown.

A cover plate 70 is then to be placed on the donor plate 64. Typically, the cover plate 70 will comprise a glass disc. One reason the cover plate 70 is made of glass as well as the receptor container 12 and the jacket 48 is so that a user can then readily observe the donor material 68, membrane 62 and whether the receptor liquid 24 is in continuous contact with the membrane 62. Also, if an air bubble happens to be resting against the membrane 62, incorrect dissolvability readings will be ascertained within the aliquots. It is important to view the membrane 62, and that is why transparent glass is used.

A cap 72 is located on the cover plate 70. Typically, the cap 72 will be constructed of a rigid metallic material with generally aluminum or stainless steel being preferred. The cap 72 includes an enlarged center hole 74. The hole 74 will permit visual observance of the cover plate 70 which is transparent and therefore can readily observe the donor material 68 to make sure that an adequate quantity of the material 68 is contained within the center opening 66. The cap 72 has a sidewall 76 that is to be positioned against the side of the annular flange 22. Typically, the cap 72 will be in the shape of a cup. The sidewall 76 includes a cutout 78. The cutout 78 is to function as a viewing port so that the user is able to observe the membrane 62 and ascertain whether there are any air bubbles located against the membrane 62. If there is determined that there is an air bubble, a measure will have to be taken to remove that bubble. Typically, the measure to remove the air bubble will be to remove the cap 76, the cover plate 70, the donor plate 64 and the membrane 62 to permit the air bubble to escape. Then the membrane 62, donor plate 64, cover plate 70 and cap 72 are then reinstalled in position.

It is desirable, and necessary, for the cap 62 to be tightly restrained in position on the annular flange 22. In order to achieve this, there is utilized a quick disconnect clamping apparatus 80. The clamping apparatus 80 comprises an upper plate 82 and a lower plate 84. The upper plate 82 is basically U-shaped defining an internal cavity 86. Similarly, the lower plate 84 is U-shaped and has an internal cavity 88. The upper plate 82 is mounted relative to the lower plate 84 by means of a pair of bolt fasteners 90 and 92. Surrounding the bolt fastener 90 is a spacer sleeve 94. A similar spacer sleeve 96 surrounds the bolt fastener 92. Spacer sleeves 94 and 96 are located between the upper plate 82 and the lower plate 84. The spacer sleeves 94 and 96 function to define the minimum spacing between the upper plate 82 and lower plate 84.

Located about the bolt fastener 90 is a coil spring 98. A similar coil spring 100 is located about the bolt fastener 92. The coil springs 98 and 100 abut against the lower plate 84. The outer end of the coil spring 98 abuts against a nut 102 that is threadably mounted on the bolt fastener 90. The outer end of the coil spring 100 abuts against a nut 104 that is threadably mounted on the bolt fastener 92. Loosening and tightening of the nuts 102 and 104 on their respective bolt fasteners 90 and 92 will control the amount of clamping force that is achieved by the clamping apparatus 80 of this invention.

The length of the spacer sleeves 94 and 96, which is identical, is preselected to be just slightly less than the distance from the bottom edge 106 of the annular flange 22 and the top of the cap 72. The upper plate 82 has, in essence, a pair of legs located on each side of the internal cavity 86. The outer end of these legs include upturn flanges 108 and 110. The lower plate 84 includes a similar pair of legs located between the internal cavity 88. Each of these legs include downturn flanges 112 and 114.

The use of the flanges 108, 110, 112 and 114 are to facilitate manual separating movement of the upper plate 82 from the lower plate 84 in order to permit its installation about the annular flange 22. Manual pressure is to be applied to the flanges 108, 110, 112 and 114. When installed, the upper plate 82 will abut against the upper surface of the cap 72 and the lower plate 84 will abut against the bottom edge 106. The biasing of the springs 98 and 100 will cause a clamping force to be applied against the cap 72 holding the cap 72 tightly in position on the annular flange 22.

When it is desired to change the membrane 62, it is only necessary to quickly grasp clamping apparatus 80 and disengage such from the annular flange 22 which will provide access to remove the cap 72, cover plate 70 and donor plate 64 to gain access to the membrane 62. Once the clamping apparatus 82 is then quickly installed back into position on the annular flange 22 and cap 72, the cap 72 is then securely held in position on the annular flange 22.

What is claimed is:

1. A diffusion cell comprising:

a main housing having a receptor chamber, said receptor chamber having an open top and a closed bottom, said receptor chamber adapted to contain a receptor liquid in sufficient quantity to connect with said open top, a receptor liquid refilling port connecting with said receptor chamber directly adjacent said closed bottom, a sampling port connecting with said receptor chamber intermediate said open top and closed bottom nearer said open top;

a thin membrane mounted on said housing extending across said open top effectively closing such;

a donor housing having a donor chamber connecting with said membrane, a media to be supplied to said donor chamber and in contact with said membrane; and a quick release clamping apparatus engaging with said donor housing functioning to tightly press said donor housing onto said membrane and said main housing.

2. The diffusion cell as defined In claim 1 wherein:

said sampling port including a capillary passage, the function of said capillary passage to minimize the residual volume of a sample that has been extracted through said sampling port.

3. The diffusion cell as defined in claim 1 wherein:

said donor housing including a disc which has a center opening, said donor housing also including a cap which is mounted onto said disc, said donor chamber being defined by said center opening.

4. The diffusion cell as defined in claim 3 wherein:

said cap including a viewing port, said viewing port to facilitate the physical examination of said membrane at said open top for the purpose of insuring that there are no air bubbles located at said open top in contact with said membrane.

5. The diffusion cell as defined in claim 1 wherein:

both said receptor liquid refilling port and said sampling port including a LUER fitting, said LUER fitting facilitating quick connection and disconnection with an appropriate liquid supply and/or discharge conduit.

6. The diffusion cell as defined in claim 3 wherein:

said quick release clamping apparatus comprising a U-shaped clamp assembly which has an open cavity, said main housing to be located within said open cavity with one plate being mounted on said main housing and the remaining said plate being mounted against said cap, said one plate and said remaining plate being spring biased toward each other when installed on said main housing applying a continuous bias tending to keep said donor housing in tight connection with said main housing.

7. A diffusion cell comprising:

a main housing having a receptor chamber, said receptor chamber having an open top and a closed bottom, said receptor chamber adapted to contain a receptor liquid in sufficient quantity to connect with said open top, a receptor liquid refilling port connecting with said receptor chamber directly adjacent said closed bottom, a sampling port connecting with said receptor chamber intermediate said open top and closed bottom but nearer said open top;

a thin membrane mounted on said housing extending across said open top effectively closing such;

a donor housing having a donor chamber connecting with said membrane, a media to be supplied to said donor chamber and in contact with said membrane; and said sampling port including a capillary passage, the function of said capillary passage to minimize the residual volume of a sample that has been extracted through said sampling port.

8. The diffusion cell as defined in claim 7 wherein:

said donor housing including a disc which has a center opening, said donor housing also including a cap which is mounted onto said disc, said donor chamber being defined by said center opening.

9. The diffusion cell as defined in claim 8 wherein:

said cap including a viewing port, said viewing port to facilitate to the physical examination of said membrane at said open top for the purpose of insuring that there are no air bubbles located at said open top in contact with said membrane.

10. The diffusion cell as defined in claim 7 wherein:

both said receptor liquid refilling port and said sampling port including a LUER fitting, said LUER fitting facilitating quick connection and disconnection with an appropriate liquid supply and/or discharge conduit.

11. A diffusion cell comprising:

a main housing having a receptor chamber, said receptor chamber having an open top and a closed bottom, said receptor chamber adapted to contain a receptor liquid in sufficient quantity to connect with said open top, a receptor liquid refilling port connecting with said receptor chamber directly adjacent said closed bottom, a sampling port connecting with said receptor chamber intermediate said open top and closed bottom but nearer said open top;

a thin membrane mounted on said housing extending across said open top effectively closing such;

a donor housing having a donor chamber connecting with said membrane, a media to be supplied to said donor chamber and in contact with said membrane; and said donor housing including a disc which has a center opening, said donor housing also including a cap which is mounted onto said disc, said donor chamber being defined by said center opening.

12. The diffusion cell as defined in claim 11 wherein:

said cap including a viewing port, said viewing port to facilitate the physical examination of said membrane at said open top for the purpose of insuring that there are no air bubbles located at said open top in contact with said membrane.

13. The diffusion cell as defined in claim 11 wherein:

both said receptor liquid refilling port and said sampling port including a LUER fittings, said LUER fitting facilitating quick connection and disconnection with an appropriate liquid supply and/or discharge conduit.

* * * * *